United States Patent [19]

Cook

[11] Patent Number: 5,907,100

[45] Date of Patent: May 25, 1999

[54] METHOD AND SYSTEM FOR DETECTING AND DISPLAYING DEFECTS IN PIPING

[75] Inventor: Patrick Cook, Skiatook, Okla.

[73] Assignee: Gas Research Institute, Chicago, Ill.

[21] Appl. No.: 08/885,367

[22] Filed: Jun. 30, 1997

[51] Int. Cl.⁶ .................................................. G01N 29/06
[52] U.S. Cl. ............................. 73/602; 73/643; 73/622; 73/623
[58] Field of Search ........................ 73/643, 597, 598, 73/599, 600, 602, 609, 610, 611, 612, 613, 614, 615, 616, 620, 622, 624, 628, 625, 644

[56] References Cited

U.S. PATENT DOCUMENTS

| | | | |
|---|---|---|---|
| 3,805,596 | 4/1974 | Klahr | 73/602 |
| 3,850,028 | 11/1974 | Thompson et al. | 73/71.5 |
| 3,885,224 | 5/1975 | Klahr | 73/602 |
| 3,986,389 | 10/1976 | Mesina et al. | 73/611 |
| 4,092,868 | 6/1978 | Thompson | 73/638 |
| 4,098,131 | 7/1978 | Renzel | 73/627 |
| 4,100,809 | 7/1978 | Bobrov et al. | 73/638 |
| 4,121,468 | 10/1978 | Glover et al. | 73/602 |
| 4,289,030 | 9/1981 | Alers et al. | 73/588 |
| 4,320,661 | 3/1982 | Peterson et al. | 73/643 |
| 4,449,411 | 5/1984 | Suhr et al. | 73/643 |
| 4,481,824 | 11/1984 | Fujimoto et al. | 73/643 |
| 4,619,143 | 10/1986 | Franken | 73/598 |
| 4,691,572 | 9/1987 | van den Berg et al. | 73/643 |
| 4,727,321 | 2/1988 | Huschelrath | 324/226 |
| 4,732,040 | 3/1988 | Boettger et al. | 73/643 |
| 4,769,598 | 9/1988 | Krieg et al. | 324/219 |
| 4,793,185 | 12/1988 | Boettger et al. | 73/643 |
| 5,085,082 | 2/1992 | Cantor et al. | 73/622 |
| 5,243,862 | 9/1993 | Latimer | 73/600 |
| 5,359,898 | 11/1994 | Latimer | 73/600 |
| 5,457,994 | 10/1995 | Kwun et al. | 73/587 |
| 5,526,691 | 6/1996 | Latimer et al. | 73/592 |
| 5,581,037 | 12/1996 | Kwun et al. | 73/623 |
| 5,619,423 | 4/1997 | Scrantz | 364/507 |
| 5,648,613 | 7/1997 | Kiefer | 73/611 |

*Primary Examiner*—Michael Brock
*Assistant Examiner*—Rose M. Miller
*Attorney, Agent, or Firm*—Pauley Petersen Kinne & Fejer

[57] ABSTRACT

A detection and imaging system 10 is provided for locating defects in pipes using electromagnetic acoustical transducer (EMAT) sensors. The system includes an ultrasonic generator 22 (FIG. 2) configured to transmit a pulse signal to the EMAT transmitter 16 (FIG. 1). The transmitter 16, in turn, sends an ultrasonic wave through a pipe 13. The EMAT receiver 18 (FIG. 1) is configured to detect the transmitted ultrasonic signal 24 and receive a reflected ultrasonic signal that is reflected by a defect in the pipe. A processor is configured to generate a filter signal based upon the transmitted ultrasonic signal 24, to correlate the filter signal and the rejected ultrasonic signal to derive the location of the defect relative to the receiver, and to display the profile of the defect.

21 Claims, 5 Drawing Sheets

METHOD AND SYSTEM FOR DETECTING AND DISPLAYING DEFECTS IN PIPING

FIELD OF THE INVENTION

The present invention generally relates to automated nondestructive defect detection systems and, more particularly, to an inline pipe detection system and method for efficiently identifying and communicating a precise location and characteristic profile of a defect in a pipe.

BACKGROUND

The need for nondestructive detection of defects in piping is necessary to avoid costly shut down of equipment and for ensuring the integrity of aged piping, specifically where, the aged piping is carrying high pressure combustible fluids and gases that are a safety hazard. The defects detected may include but are not limited to flaws such as cracks, dents and pits.

One embodiment of such a system uses multiple ultrasonic piezoelectric transducers mounted inside a liquid filled elastomer "wheel." This system transmits an ultrasonic wave that is refracted at the elastomer/pipe wall interface and is subsequently guided by the pipe wall.

When the compressional wave (the p-wave) produced by the transducer and, transmitted by the liquid in the wheel, reaches the interface between the wheel elastomer and the steel pipe wall, some of the p-wave energy is converted to vertically polarized shear waves (Sv waves) and continues to travel in the pipe wall until it encounters some type of defect within the pipe wall. The defect may be a crack, an inclusion, a lamination, or other defect. When the Sv wave encounters the defect, a portion of the energy is reflected back along the same raypath to the transducer which, in the meantime, is converted from a transmitter to a receiver. The reflected signal is then indicated by an electrical pulse or waveform at the transducer terminals. The initial processing is simiplistic; if no signal is received during the "on time", which is the time that the transducer functions as a receiver, then the decision is "no defects in the raypath" for that segment of the pipeline. However, if a reflected signal is received, then the decision is "a defect present in the raypath" of the Sv wave. At this point, the process becomes more complex; the user must now decide if the defect detected is one of interest such as a crack or something relatively benign such as a lamination. Considerable effort has gone into the process of discriminating specific types of defects. Unfortunately, only one company has claimed satisfactory success in defect discrimination and the details remain unavailable to those outside that organization.

A second embodiment utilizing ultrasound also employs piezoelectric transducers. However, instead of using a liquid filled wheel to "couple" the ultrasound to the pipe wall, the line is flooded with a suitable liquid in order to provide a means for transferring the ultrasonic energy into the steel pipe wall. Moreover, in order to make the system effective for crack detection, the transducers are mounted at an angle with respect to a plane tangent to the pipe wall at a point directly over the transducer in the radial direction. Consequently, the identical effect discussed in the previous embodiment is similarly implemented. Namely, the ultrasonic p-wave travels through the liquid medium and strikes the pipe wall at the Brewster angle. When this happens, part of the incident energy is converted to an Sv wave and continues to travel as such in the pipe wall. When an defect is encountered, part of the energy is reflected from the defect and, again, travels back along the original path to the transducer. At the transducer, a defect is noted when an electrical pulse or waveform is present at the transducer terminals. The processing of the results suffer the same difficulties as that discussed in the previous embodiment. There are considerable difficulties in discriminating the specific types of defects. Fundamentally, there are no reliable methods existing in the public domain.

The following are additional disadvantages of the second embodiment. First, the transducer angle must be maintained during the complete transmit/receive cycle; otherwise, the signal will not be detected even if a defect is present. Second, the pipeline must either be filled with a suitable liquid, all liquids are not suitable, for the couplant, or the device must be operated in a "slug" of liquid maintained between batching pigs, which is no small task. Third, neither of the techniques discussed above, filling the pipe with a suitable liquid, or operating in a "slug", are not readily acceptable to gas pipeline operators. Fourth, the large number of transducers lead to serious problems; since, transducer reliability leaves much to be desired and the maintenance can be onerous. Finally, the large number of transducers translates to a high quantity of data to be processed; hence, this system is infamous for creating huge data files, many gigabytes.

Consequently, based on the deficiencies of the prior art discussed above, a need has developed in the art for a defect detection system and method, which is inexpensive to implement, utilizes a minimum number of transducers, is capable of detecting defects in both liquid and gas piping, and can generate an enhanced characteristic representation of the defect. By generating an enhanced characteristic representation, the defect detection system and method facilitates discrimination of the defect.

SUMMARY OF INVENTION

The present invention provides a system and method for detecting defects in pipe using electromagnetic acoustic transducer (EMAT) sensors. Briefly described, the system is composed of an EMAT transmitter, an EMAT receiver, a firing pulse generator, a master processor, digital signal processor, odometer processor, and data acquisition and processing software.

The pulse generator drives the transmitter, which causes a direct wave to propagate internally through the span of the pipe. After the direct wave has moved past the receiver, the data acquisition system digitizes the receiver data, that is produced by the receiver, for a fixed period of time. This period of time is referred to as the "reflection window" and contains a fixed number of samples referred to as the reflection vector, or signal vector. This process is repeated at a fixed distance increment as the sensors are moved down the pipe. The end result is a series of reflection vectors or an array of data which represent the path along the pipe.

The reflection vector is then processed through matched filters, one generated by a sine function and the other a cosine function, to develop a correlation vector. The correlation vector will have positive peaks where the signal vector and the matched filters are aligned. Based on the positive peaks, a peak vector is defined using three running averages of the correlation vector and a peak selection algorithm.

A two-dimensional gray-scale image of the inspected area can be drawn using the series of peak vectors and the corresponding correlation vector magnitude. The horizontal direction represents the series of peak vectors or the longitudinal direction along the pipe. The vertical direction represents the length of the peak vector or the circumferential direction around the pipe. By scaling the distance that the peak vectors are displayed based on the velocity of the wave packet, a geometrically correct image can be drawn. The peak vectors are plotted using the corresponding correlation vector magnitude to determine the shade of gray in which it will be displayed. The higher the correlation magnitude, the darker the gray-scale. This allows the observer to distinguish large reflections from small ones. In other words, the bigger and deeper the defect, the darker the gray-scale will be. A single trace characteristic profile of the area can be drawn by plotting the maximum correlation magnitude of each correlation vector.

The invention can also be generally conceptualized as providing a methodology for detecting and imaging defects in pipe using EMAT transducers and digital signal processing techniques. In this regard, the method can be broadly summarized as a detection method for locating defects in pipes using ultrasonic waves, comprising the steps of: transmitting an ultrasonic signal through a pipe; receiving a reflected ultrasonic signal that is reflected by a defect in the pipe based upon the transmitted ultrasonic signal; generating a filter signal based upon the transmitted ultrasonic signal; correlating the filter signal and the reflected ultrasonic signal to derive the location of the defect relative to the detector; and correlating the filter signal and the reflected ultrasonic signal to derive the profile of the defect.

The invention has many advantages, a few of which are delineated hereafter as examples.

An advantage of the invention is that it provides for nondestructive detection of defects in pipes.

Another advantage of the invention is that it increases the efficiency in detecting defects in a nondestructive detection system.

Another advantage of the invention is that it reduces the complexity of a nondestructive detection system.

Another advantage of the invention is that it reduces the number of transducers necessary for effective detection of defects.

Another advantage of the invention is that it provides accurate determination of the location and profile of the defect.

Another advantage of the invention is that it provides for a reliable system that is simple in design and easily operated.

Another advantage of the invention is that it provides an inexpensive system and method for nondestructive detection of defects in piping.

Other objects, features, and advantages of the present invention will become apparent from the following specification, when read in conjunction with the accompanying drawings. All such additional objects, features, and advantages are intended to be included herein.

BRIEF DESCRIPTION OF THE DRAWINGS

The present invention can be better understood with reference to the following drawings. The drawings are not necessarily to scale, emphasis instead being placed upon clearly illustrating principles of the present invention.

DETAILED DESCRIPTION OF THE PREFERRED EMBODIMENT

The features and principles of the present invention will now be described relative to a preferred embodiment thereof. It will be apparent to those skilled in the art that numerous variations or modifications, including software and hardware, may be made to the preferred embodiment without departing from the spirit and scope of the present invention. Thus, such variations and modifications are intended to be included herein within the scope of the present invention, as set forth in the claims.

System Architecture

Figure 1:
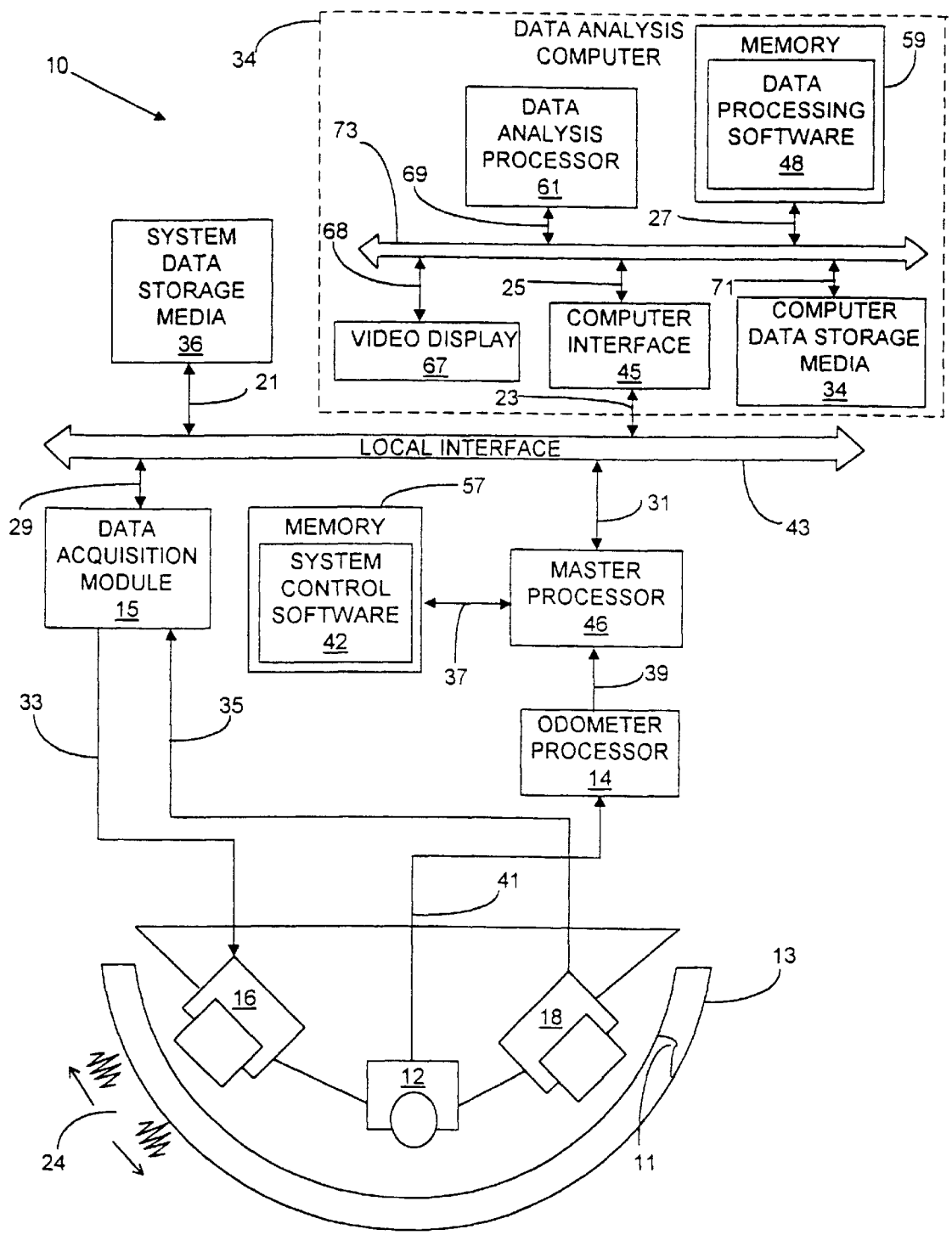
FIG. 1 is a high level schematic diagram of the defect detection and imaging system of the invention.

Referring now in more detail to the drawings, wherein like reference numerals designate corresponding parts throughout the several figures, FIG. 1 is a schematic block diagram of the defect detection and imaging system 10 of the present invention. The hardware of the preferred embodiment of the system 10 includes the following components. An odometer 12 that is connected to odometer processor 14, which can be, for example, any suitable general purpose microprocessor. The odometer 12, in the preferred embodiment, can be any suitable odometer of a variety that are well known in the art. The odometer 12 and odometer processor 14 are electrically coupled as indicated by reference arrow 41 and are responsible for determining the location, longitudinally along the pipe 13, of the EMAT transmitter 16 and receiver 18. The location of the transmitter 16 and receiver 18 is communicated to the master processor 46 by the odometer processor 14. The master processor may be any suitable general purpose microprocessor, but is a model ZT 6500 microprocessor in the preferred embodiment that is manufactured by and is commercially available from Ziatech Corp. In the preferred embodiment, the signal transfer is accomplished through an electrical coupling 39 utilizing parallel communications. This communication may also be accomplished using other communication types that are well known in the art.

Once the signal from the odometer processor 14 is detected by the system control software 42, the system control software 42 is configured to send a signal through electrical coupling 31 and the local interface 43, to the data acquisition module 15 to initiate a pipe inspection cycle. The system control software 42 is stored in memory 57 and is accessed through an electrical coupling (e.g., one or more buses) 37 by the master processor 46. In the preferred embodiment, the memory 57 can be any commercially available disk drive, tape, or flash memory.

After the data acquisition module receives the digital initiation signal over the local interface 43 and electrical coupling 29, the data acquisition software 38 (FIG. 2), which is stored in memory 63 (FIG. 2) and accessed and executed by the digital signal processor (DSP) 32 (FIG. 2) through electrical coupling 53 (FIG. 2), will initiate a pipe section scan. The memory 63 in the preferred embodiment is internal to the DSP 32. The DSP 32, can be any suitable general purpose microprocessor, but is a Snaggletooth Compact PCI™ processor in the preferred embodiment that is manufactured by and commercially available from Bittware Research Systems.

During a pipe section scan, the DSP 32 (FIG. 2), operating under the control of the data acquisition software 38 (FIG. 2), is designed to activate the chirp pulse generator through electrical coupling 55. The chirp pulse generator 22 (FIG. 2) provides the drive pulse, through electrical coupling 33, to the EMAT transmitter 16, thereby inducing an ultrasonic wave 24 into the pipe. The ultrasonic wave travels around the circumference of the pipe 13 (FIG. 1) past the receiver.

Figure 2:
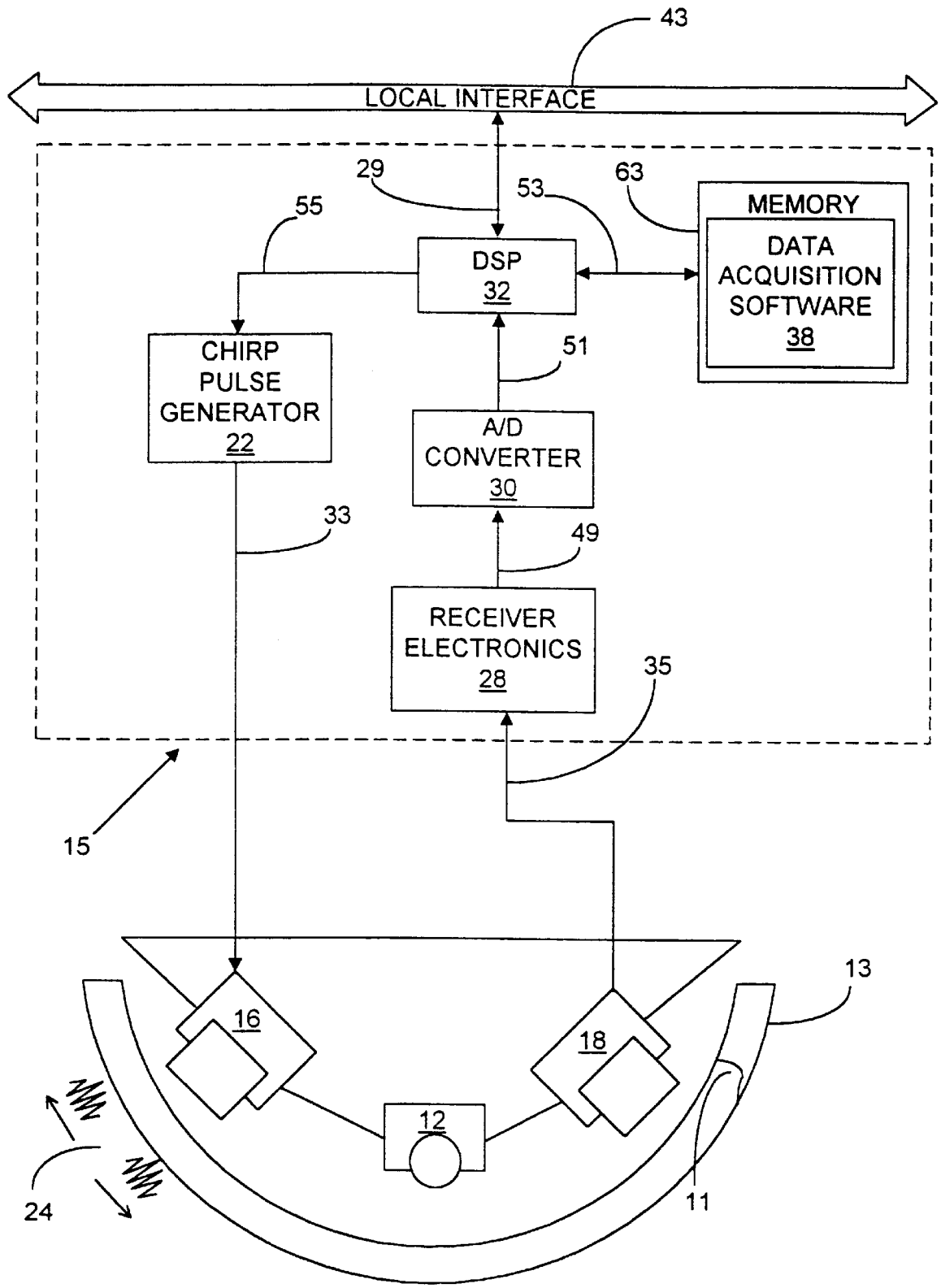
FIG. 2 is a detailed schematic diagram of the data acquisition module of FIG. 1.

After expiration of a delay period, started at the firing of the chirp pulse generator 22 (FIG. 2), the DSP 32 (FIG. 2) and data acquisition software 38 (FIG. 2) are designed to initiate a data acquisition window. During the data acquisition window, the EMAT receiver 18 is designed to capture, through its associated signal conditioning electronics 28 (FIG. 2), analog-to-digital converter (ADC) 30 (FIG. 2), and electrical couplings 35, 49 (FIG. 2), any transmitted ultrasonic wave reflected by any defect in the pipe. In the preferred embodiment, the ADC 30 is commercially available from Bittware Arrow. However, it is well known to those skilled in the art that the signal processing provided by the signal conditioning electronics and ADC 30 may be accomplished through many other different means. The resulting digital data is sampled by the DSP 32 through electrical coupling 51 (FIG. 2) and the data acquisition software 38 (FIG. 2).

At the end of the data acquisition window, the DSP 32 (FIG. 2) is designed to signal the master processor 46 (FIG. 1) through electrical coupling 29 (FIG. 1) and the local interface 43 (FIG. 1). The master processor 46 is designed to then transfer the digital data from the DSP 32 (FIG. 2) to the data storage media 36 (FIG. 1) through the system control software 42 (FIG. 1), local interface 43, and electrical coupling 21 (FIG. 1). In the preferred embodiment, the data storage media 36 is any disk drive, tape unit, flash memory, or any device capable of storing digital data.

After all pipe scans have been executed and stored in the data storage media 36 (FIG. 1), the data analysis computer 34 (FIG. 1) is designed to initiate the digital data transfer from the system data storage media 36 to computer data storage media 44 (FIG. 1). In the preferred embodiment, the computer data storage media 44 is any disk drive, tape unit, flash memory, or any device capable of storing digital data. The digital data is transferred through the local interface 43 and electrical coupling 23 (FIG. 1) to a computer interface 45 (FIG. 1). Through electrical couplings 25, 71 (FIG. 1), and digital communications bus 73 (FIG. 1), the computer interface 45 is designed to delivery the digital data to the computer data storage media 44. In the preferred embodiment, the computer interface is an Ethernet card model ZT 6650 manufactured by and commercially available from Ziatech Corporation. However, the computer interface may be any means known in the art for interfacing a general purpose computer to a digital communications network.

The data analysis computer 34 (FIG. 1), which in the preferred embodiment is any general purpose computer, is designed to access through electrical coupling 27 (FIG. 1) and the digital communications bus 73 (FIG. 1) the data processing software 48 (FIG. 1). The data processing software is stored in memory 59 (FIG. 1). In the preferred embodiment, the memory is part of the data analysis computer 34. However, it is well known in the art that the memory 59 may be a self contained module accessed through an electrical coupling. The data analysis computer's processor 61 (FIG. 1), executing the data processing software 48, is designed to process the sampled digital data stored in computer data storage media 44 (FIG. 1). The results of the data processing software are then displayed, through electrical coupling 68 (FIG. 1) and the digital communications bus 73, on the video display 67 (FIG. 1). In the preferred embodiment the video display may be any means known to one of ordinary skill in the art for displaying digital data.

The system control software 42 (FIG. 1), data acquisition software 38 (FIG. 2), and data processing software 48 (FIG. 1) can all be stored on any computer-readable medium for use by or in connection with a computer-related system or method. In the context of this document, a computer-readable medium is an electronic, magnetic, optical, or other physical device or means that can contain or store a computer program for use by or in connection with a computer-related system or method.

System Operation

Figure 3:
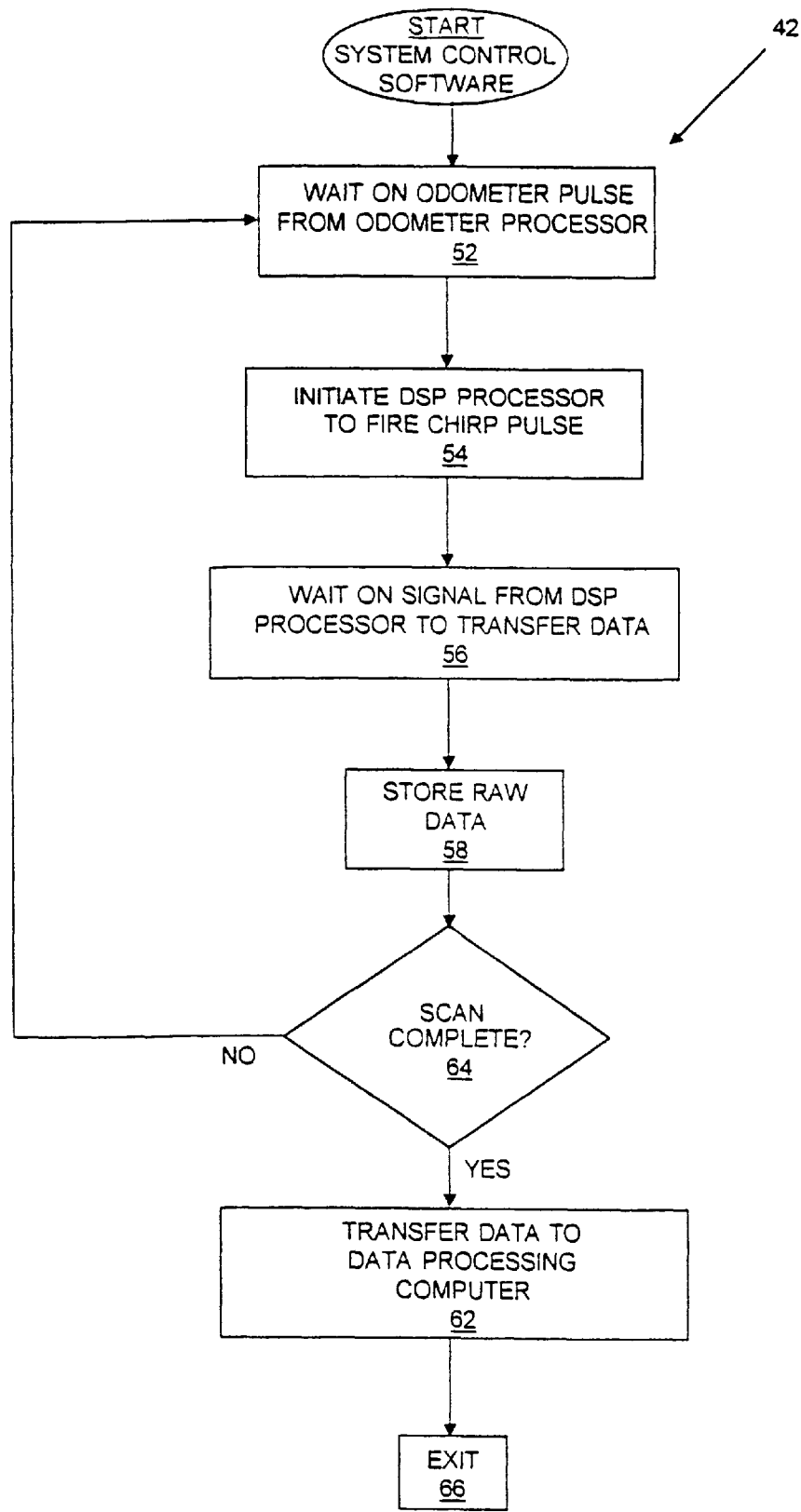
FIG. 3 is a flow chart of the system control software, which is executed by the master processor, both of FIG. 1.

In operation, as illustrated in FIG. 3, the master processor 46 (FIG. 1) waits for an odometer processor pulse 52, which is initiated by the odometer 12 (FIG. 1), in order to start the control sequence. The odometer 12 and the odometer processor 14 (FIG. 1) are responsible for signaling the location of the EMAT transmitter 16 (FIG. 1) and receiver 18 (FIG. 1) as they travel longitudinally along the pipe. This signal is received by the master processor 46 and system control software 42 (FIG. 1), which in turn will command the digital signal processor 54 through its data acquisition software 38 (FIG. 1) to initiate the chirp pulse generator 22 (FIG. 1). The chirp pulse generator 22 provides the drive pulse to the EMAT transmitter 16 for developing the ultrasonic wave 24 (FIG. 1). At this stage, the master processor 46 delegates control to the digital signal processor (DSP) and waits for a signal from the DSP to transfer data 56.

Figure 4:
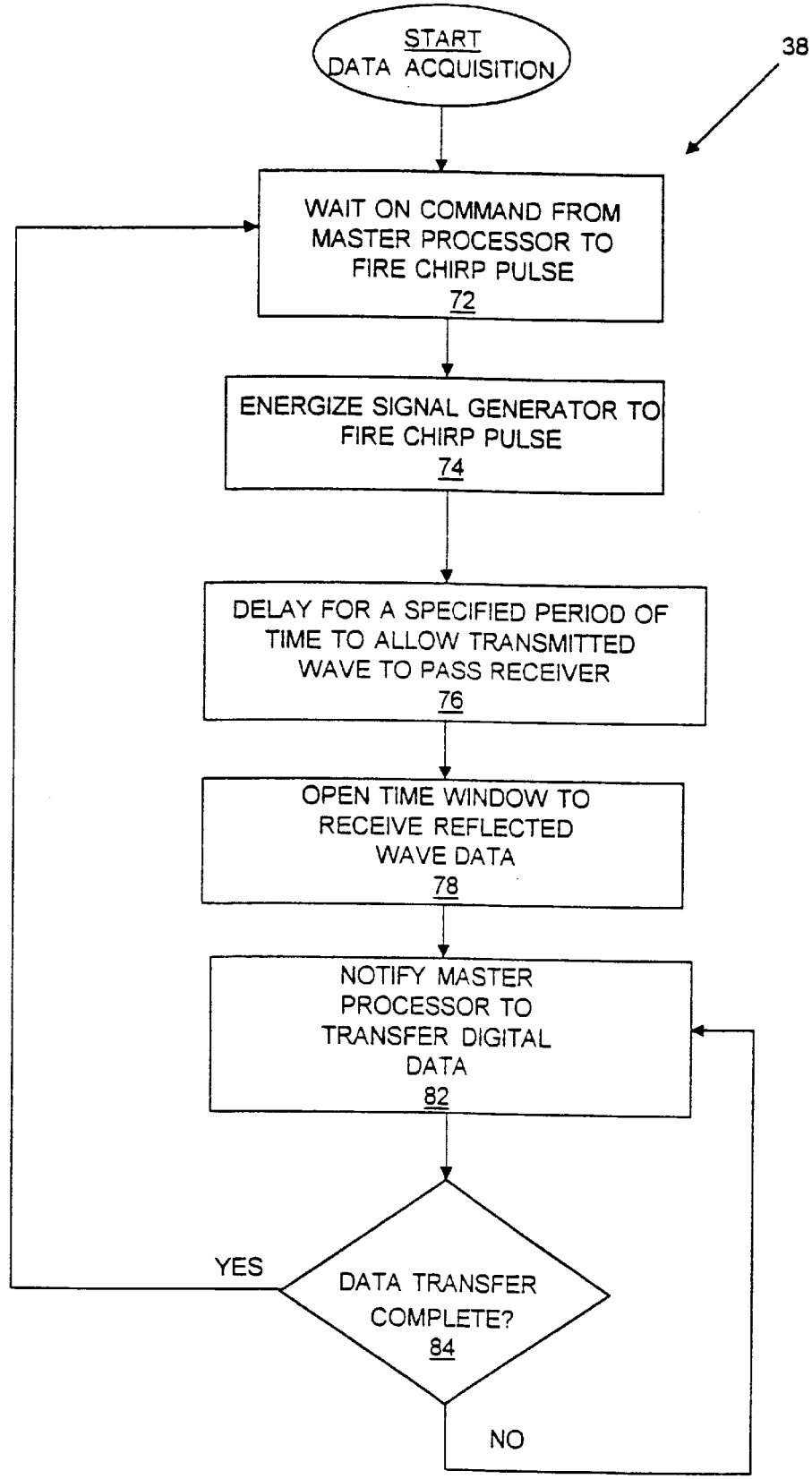
FIG. 4 is a flow chart of the data acquisition software, which is executed by the digital signal processor, both of FIG. 1.

Once the digital signal processor 32 (FIG. 1) and data acquisition software 38 (FIG. 1), illustrated in FIG. 4, receive the fire chirp pulse command 72, the chirp pulse generator 22 (FIG. 1) will be energized 74. The DSP 32 (FIG. 2) and data acquisition software 38 (FIG. 2) will now delay for a specified time period for the transmitted ultrasonic to pass the EMAT receiver 18 (FIG. 1) 76. The expiration of the delay will open a data acquisition window or time 78. During the data acquisition window, the EMAT receiver 18 (FIG. 1) and associated electronics 28 (FIG. 1) will capture any transmitted ultrasonic waves reflected by any defects in the pipe. The received reflected wave is processed by an analog to digital converter 30 (FIG. 1), before the resulting digital data is transferred to the digital signal processor 32. The digital data signal processor 32 and data acquisition software 38 provide a means for transferring the sampled data, under the control of the master processor 82 and system control software 42 (FIG. 1), to the data storage media 36 (FIG. 1) and the data analysis computer 34 (FIG. 1). After the master has been notified and the data transfer has been completed 82, 84, the DSP 32 data acquisition software 38 will reset and wait for another command from the master processor to fire the chirp pulse 72. This will begin another pipe segment inspection.

The master processor 46 (FIG. 1) and system control software 42 (FIG. 1) will store the digital data 58 (FIG. 3) in the system data storage media 36 (FIG. 1). The system control software 42 (FIG. 1) will then determine whether the entire pipe scan has been completed and exit the control loop or whether additional odometer pulses will be processed 64, 66 (FIG. 3).

Figure 5:
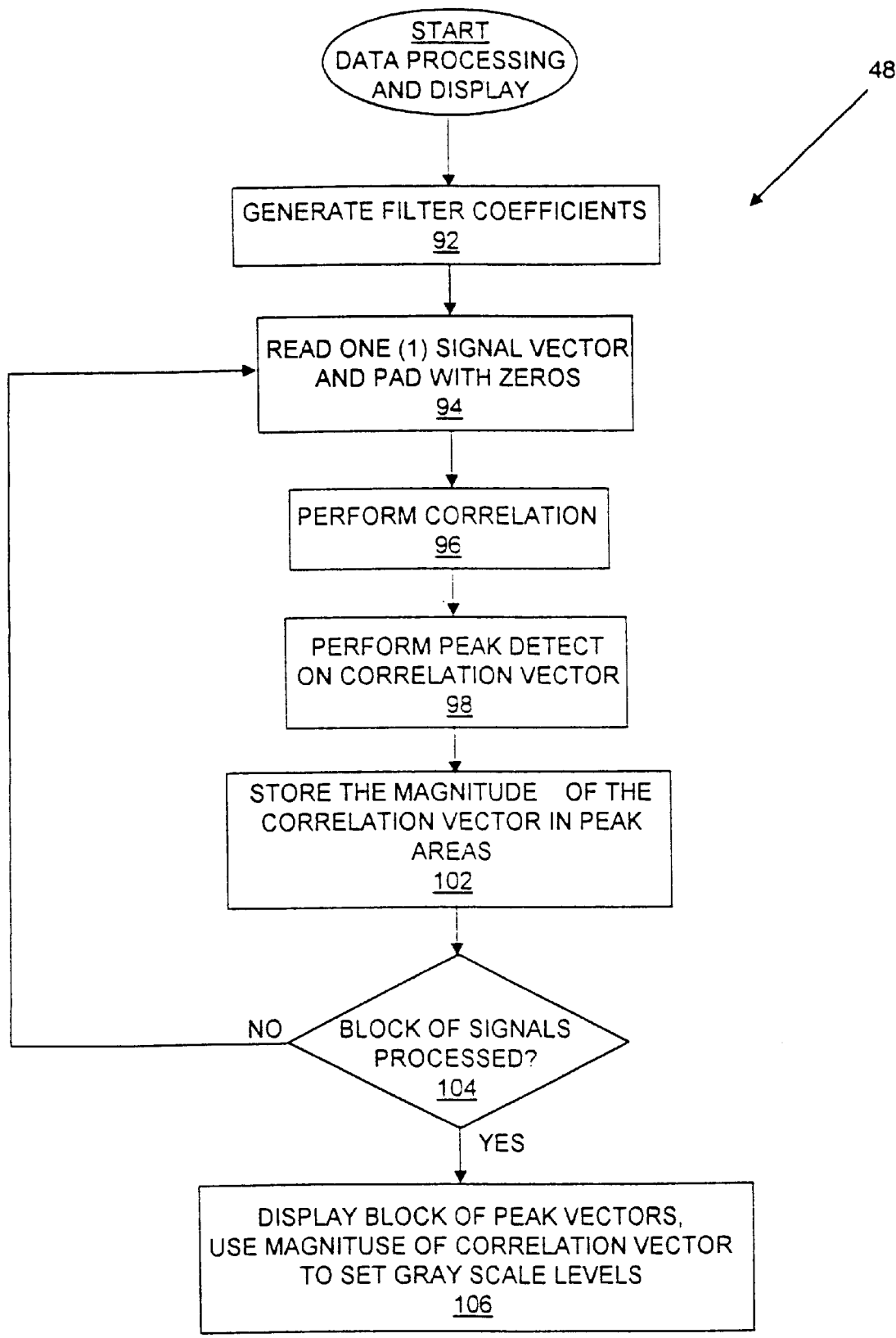
FIG. 5 is a flow chart of the data processing and display software, which executed by the data analysis computer, both of FIG. 1.

After all pipe scans have been executed and stored in the data storage media 36 (FIG. 1), the data analysis computer 34 (FIG. 1) is designed to initiate the digital data transfer from the system data storage media 36 to computer data storage media 44 (FIG. 1). In the final stage, the data analysis computer 34 (FIG. 1) and the data processing software 48 (FIG. 1) will process the data stored in the computer data storage media 44. As illustrated by the flow chart in FIG. 5, the data processing software 48 will generate the digital filter coefficients 92, utilized by the matched digital cosine and sine software filters, using the following equations:

$$a(k)=X^*\cos(2\pi(f_0+(k^*df))^*k^*dt) \quad k=0,1,2,\ldots N \quad (1.0)$$

$$b(k)=X^*\sin(2\pi(f_0+(k^*df))^*k^*dt) \quad k=0,1,2,\ldots N \quad (2.0)$$

where X is the amplitude scaling factor, $f_0$ is the starting frequency, df is the change in frequency per step, dt is the time interval per step, and N is the length of the filter. The coefficients are windowed using a Welch windowing technique. The windowing is softened by adding 5 to the sample number (k) and 10 to the number of filter samples (N). The following equations are used to window the coefficients:

$$A(k)=a(k)^*[1-(((k+5)-(0.5^*(N+9)))/(0.5^*(N+11)))^2]$$
$$k=0,1,2,\ldots,N \quad (3.0)$$

$$B(k)=b(k)^*[1-(((k+5)-(0.5^*(N+9)))/(0.5^*(N+11)))^2]$$
$$k=0,1,2,\ldots,N \quad (4.0)$$

Following the development and windowing of the filter coefficients, a signal or refection vector is read and padded with zeros 94. A zero pad that is one half of the filter length (N) is added to the beginning and end of the reflection vector. Then the correlation vector is calculated 96 with the following equation:

$$C(k) = \sum_{j=0}^{N-1} \sqrt{(A_j * S_{(j+k)})^2 + (B_j * S_{(j+k)})^2} \quad k = 0,1,2\ldots, M-N \quad (5.0)$$

where S is the reflection vector and M is the length of the reflection vector (including the zero pad). The correlation vector will have positive going peaks where the signal vector and the matched filters are aligned. Next a peak vector is derived from the correlation vector. The peak vector represents the arrival times of the echoes based on the peaks of the correlation vector. The peak detect 98 uses 3 running averages to determine peak areas. The three running averages are defined as:

$$PRE(k)=((C_k+C_{(k+1)}+C_{(k+2)}+C_{(k+3)})/4)+Y \quad k=0,1,2,\ldots M-16 \quad (6.0)$$

$$CNTR(k)=((C_{(k+6)}+C_{(k+7)}+C_{(k+8)}+C_{(k+9)})/4)+Y$$
$$k=0,1,2,\ldots M-16 \quad (7.0)$$

$$POST(k)=((C_{(k+12)}+C_{(k+13)}+C_{(k+14)}+C_{(k+15)})/4)+Y$$
$$k=0,1,2,\ldots M-16 \quad (8.0)$$

where Y is a constant. The peak vector is defined as 1 if the center average is greater than the pre and post averages. It is defined as 0 if the center average is greater than the pre and post averages. The Y constant defines how sharp of a peak is required in the correlation vector to get a peak indication in the peak vector. The following statements summarize the peak vector:

$$P(k)=0 \text{ If } CNTR(k)>PRE(k) \text{ AND } CNTR(k)>POST(k) \quad (9.0)$$

$$P(k)=1 \text{ If } CNTR(k)<PRE(k) \text{ AND } CNTR(k)<POST(k) \quad (10.0)$$

The corresponding magnitude of the correlation vector in the peak areas are also identified and stored 102.

After the block of signal vectors have been processed 104, a two-dimensional gray-scale image of the inspected area can be drawn, on an external communications source 44 (FIG. 1), using the series of peak vectors and the corresponding correlation magnitude. In the preferred embodiment, the external communications source is a video display. The horizontal direction on the display represents the series of peak vectors or the longitudinal direction along the pipe. The vertical direction represents the length of the peak vector or the circumferential direction around the pipe. By scaling the distance that the peak vectors are displayed based on the velocity of the wave packet, a geometrically correct image can be drawn. The peak vectors are plotted using the corresponding correlation magnitude to determine the gray-scale 106. The higher the correlation magnitude, the darker the gray-scale for the defect will be. This allows the observer to sort large reflections from small ones. In other words, the bigger and deeper the defect, the darker the gray-scale should be. A single trace characteristic profile of the area can be drawn by plotting the maximum correlation magnitude of each correlation vector.

What is claimed is:

1. A detection system for locating defects in pipes using ultrasonic waves, comprising:

an ultrasonic generator configured to transmit an ultrasonic signal through a pipe, said ultrasonic generator configured to produce a linear chirp firing pulse and including a linear chirp coil adapted to receive said firing pulse and produce said transmitted ultrasonic signal therefrom;

an ultrasonic receiver configured to detect said transmitted ultrasonic signal and receive a reflected ultrasonic signal that is reflected by a defect in said pipe; and a processing logic configured to generate a filter signal based upon said transmitted ultrasonic signal and configured to correlate said filter signal and said reflected ultrasonic signal to derive a location of said defect relative to said detector.

2. The system of claim 1, further comprising an indicator configured to indicate to a user said location of said defect.

3. The system of claim 1, wherein said generator and said detector are disposed on an external surface of said pipe.

4. The system of claim 1, wherein said generator and said detector are disposed on an internal surface of said pipe.

5. The system of claim 1, wherein said generator and said detector are disposed on opposite surfaces of said pipe.

6. The system of claim 1, wherein said generator and said detector are an electromagnetic acoustic transducer.

7. The system of claim 1, wherein said processing logic comprises: digital sine and cosine filters based upon said transmitted ultrasonic signal.

8. The system of claim 2, wherein said indicator is a graphical computer interface.

9. A detection system for locating defects in pipes using ultrasonic waves, comprising:

an ultrasonic generator configured to transmit said ultrasonic signal through a pipe, said ultrasonic generator configured to produce a linear chirp firing pulse and including a linear chirp coil adapted to receive said firing pulse and produce said transmitted ultrasonic signal therefrom;

an ultrasonic receiver configured to detect said transmitted ultrasonic signal and receive a reflected ultrasonic signal that is reflected by said defect in said pipe;

a processing logic configured to generate a filter signal based upon said transmitted ultrasonic signal and configured to correlate said filter signal and said reflected ultrasonic signal to derive a location of said defect relative to said detector; and said processing logic further configured to correlate said filter signal and said reflected ultrasonic signal to derive a profile of said defect.

10. A detection system for locating defects in pipes using ultrasonic waves, comprising:

an ultrasonic generating means for transmitting an ultrasonic signal through a pipe, said ultrasonic generating means configured to produce a linear chirp firing pulse and including a linear chirp coil adapted to receive said firing pulse and produce said transmitted ultrasonic signal therefrom;

a receiving means for receiving a reflected ultrasonic signal that is reflected by a defect in said pipe based upon said transmitted ultrasonic signal;

a signal processing means for processing said reflected ultrasonic signal to determine a correlation vector and a peak vector; and an imaging means for displaying a two-dimensional gray image of said defect of said pipe based upon said correlation vector and said peak vector.

11. A detection method for locating defects in pipes using ultrasonic waves, comprising the steps of:

transmitting an ultrasonic signal through a pipe by means of an ultrasonic generator configured to produce a linear chirp firing pulse, said ultrasonic generator including a linear chirp coil adapted to receive said firing pulse and produce said transmitted ultrasonic signal therefrom;

receiving a reflected ultrasonic signal that is reflected by a defect in said pipe based upon said transmitted ultrasonic signal;

generating a filter signal based upon said transmitted ultrasonic signal;

correlating said filter signal and said reflected ultrasonic signal to derive a location of said defect relative to said detector; and correlating said filter signal and said reflected ultrasonic signal to derive a profile of said defect.

12. The method of claim 11, further comprising the step of indicating via a user device said location of said defect.

13. The method of claim 11, further comprising the step of indicating via a user device said profile of said defect.

14. The method of claim 11, further comprising the steps of:

transmitting said transmitted ultrasonic signal from a first position outside said pipe; and receiving said reflected signal from a second position outside said pipe wall.

15. The method of claim 11, further comprising the steps of:

transmitting said transmitted ultrasonic signal from a first position inside said pipe; and receiving said reflected signal from a second position inside said pipe wall.

16. The method of claim 11, further comprising the steps of:

transmitting said transmitted ultrasonic signal from a first position inside said pipe; and receiving said reflected signal from a second position outside said pipe wall.

17. The method of claim 11, further comprising the steps of:

transmitting said transmitted ultrasonic signal from a first position outside said pipe; and receiving said reflected signal from a second position inside said pipe wall.

18. The method of claim 11, further comprising the steps of:

generating said transmitted ultrasonic signal with a transmit electromagnetic acoustic transducer; and receiving said reflected ultrasonic signal with a receive electromagnetic acoustic transducer.

19. The method of claim 11, further comprising the step of displaying on a screen said location of said defect.

20. The method of claim 11, further comprising the step of displaying on said screen said profile of said defect.

21. A computer readable medium comprising a program for locating defects in pipes using ultrasonic waves, comprising:

means for producing linear chirp firing pulses for activating an ultrasonic generator including a linear chirp coil adapted to produce a transmitted ultrasonic signal from the linear chirp firing pulses;

means for generating filter signals based upon said transmitted ultrasonic signal;

means for correlating said filter signals and a reflected ultrasonic signal to derive a location of said defect; and means for correlating said filter signals and said reflected ultrasonic signal to derive a profile of said defect.

* * * * *